US008414771B2

(12) United States Patent
Stuart

(10) Patent No.: US 8,414,771 B2
(45) Date of Patent: Apr. 9, 2013

(54) ADVANCED BIOREFINERY PROCESS

(75) Inventor: Earnest Stuart, Lansing, MI (US)

(73) Assignee: RA Energy, East Lansing, MI (US)

( * ) Notice: Subject to any disclaimer, the term of this patent is extended or adjusted under 35 U.S.C. 154(b) by 0 days.

(21) Appl. No.: 13/368,813

(22) Filed: Feb. 8, 2012

(65) Prior Publication Data

US 2012/0201947 A1    Aug. 9, 2012

Related U.S. Application Data

(63) Continuation of application No. 12/439,345, filed as application No. PCT/US2007/077388 on Aug. 31, 2007, now Pat. No. 8,133, 393.

(60) Provisional application No. 60/841,374, filed on Sep. 1, 2006, provisional application No. 60/928,092, filed on May 8, 2007.

(51) Int. Cl.
*C02F 3/00* (2006.01)
(52) U.S. Cl. ........................................ 210/606
(58) Field of Classification Search ............ 210/606, 210/173
See application file for complete search history.

(56) References Cited

U.S. PATENT DOCUMENTS

| 4,981,592 | A | * | 1/1991 | Garbutt et al. ............... 210/606 |
| 4,997,665 | A |   | 3/1991 | Grethlein |
| 5,125,977 | A |   | 6/1992 | Grohmann et al. |
| 5,221,357 | A |   | 6/1993 | Brink |
| 5,282,980 | A |   | 2/1994 | Kew et al. |
| 5,338,366 | A |   | 8/1994 | Grace et al. |
| 5,370,999 | A |   | 12/1994 | Stuart |
| 5,562,777 | A |   | 10/1996 | Farone et al. |
| 6,635,178 | B2 |   | 10/2003 | Bowman et al. |
| 8,123,864 | B2 | * | 2/2012 | Christensen et al. ........... 127/37 |
| 8,133,393 | B2 | * | 3/2012 | Stuart ........................ 210/606 |
| 2007/0278157 | A1 | * | 12/2007 | Walsem et al. ............... 210/702 |
| 2011/0201766 | A1 | * | 8/2011 | Bergman et al. ............... 526/64 |

* cited by examiner

*Primary Examiner* — Chester Barry
(74) *Attorney, Agent, or Firm* — Kagan Binder, PLLC

(57) ABSTRACT

The present invention is a method for refining native biomass to extremely fine and highly disrupted particles using high shear and/or cavitation in combination with high temperature and high or low pH conditions which dissolve biomass to a high percentage. The method of the present invention results in a high percentage of hydrolysis, in many cases near theoretical levels, in short residence times while minimizing inputs over other methods, using low chemical inputs, and optionally with no chemical inputs in certain stages compared to existing processes. The method of the present invention also uses minimal electrical energy inputs and conserves heat energy within the process and reduces equipment requirements while producing concentrated products.

19 Claims, 4 Drawing Sheets

ADVANCED BIOREFINERY PROCESS

CROSS-REFERENCE TO RELATED APPLICATIONS

The present application is a continuation of Ser. No. 12/439,345, filed Feb. 27, 2009, now U.S. Pat. No. 8,133,393, issued Mar. 13, 2012, which is a National Phase filing under 35 USC 371 of PCT/US07/077388, filed Aug. 31, 2007 which in turn claims priority under 35 U.S.C. §119(e) to U.S. Provisional Application No. 60/841,374, filed Sep. 1, 2006, and U.S. Provisional Application No. 60/928,992, filed May 8, 2007, all of which are incorporated herein by reference in their entireties.

BACKGROUND OF THE INVENTION

1. Field of the Invention

The present invention relates to methods of refining biomass. More specifically, the present invention relates to methods of disrupting the cellular structure of biomass and conditions to hydrolyze biomass while conserving and reducing process energy and minimizing equipment required while creating highly concentrated products in short timeframes.

2. Description of the Related Art

At present, the United States produces ethanol from starch-containing corn seed using amylase enzymes to dissolve the starch to fermentable sugars, which are then fermented to ethanol using yeast. In general, while the starch in the corn seed is used in the production of ethanol, the remainder of the corn plant biomass from which the seed is extracted, i.e., the leaves, cobs and stalks, is not presently used to produce ethanol because of the lack of a practical process associated with dissolving the non-starch corn components to fermentable sugars. Thus, the ligno-cellulosic components of corn biomass represent a tremendous source of untapped energy that remains unused because of the difficulty and cost of converting it to fermentable sugars. However, from a broader biomass perspective, corn stalks and cobs represent only a small portion of biomass feedstock potential world wide. For example, the volume and cost of tropical grasses grown in poor countries could provide sugars sufficient to produce tens of billions of gallons of biofuels if a practical process existed.

Currently, there are four main technologies being researched to convert cellulose to fermentable sugars, with none of them enjoying large scale commercialization. These are: concentrated acid hydrolysis, dilute acid hydrolysis, biomass gasification and fermentation, and enzymatic hydrolysis.

Concentrated acid easily dissolves biomass. Separation of acid from sugars and acid recovery are critical operations whose cost has prohibited widespread use of concentrated acid. The concentrated sulfuric acid process has been commercialized in the past, particularly in the former Soviet Union, Germany, and Japan during wartime. Dilute acid hydrolysis occurs in two stages to maximize sugar yields from the hemicellulose and cellulose fractions of biomass. The first stage is operated under milder conditions to hydrolyze hemicellulose, while the second stage is optimized to hydrolyze the more resistant cellulose fraction. Liquid hydrolyzates are recovered from each stage, pH neutralized, and fermented to ethanol. However, these processes were only successful during times of national crisis, when economic competitiveness of ethanol production could be ignored.

In biomass gasification and fermentation, biomass is converted to a synthesis gas, which consists primarily of carbon monoxide, carbon dioxide, and hydrogen via a high temperature gasification process. Anaerobic bacteria are then used to convert the synthesis gas into ethanol. A practical combination of mechanico-chemical treatments and enzymes has not been commercialized, although some highly subsidized operations are being funded by the U.S. government with some private capital.

Biomass structures are naturally resistant to penetration by low levels of chemicals and/or process heat transfer, or to enzymatic hydrolysis, thus requiring high and uneconomical levels of those inputs to achieve high levels and fast rates of hydrolysis, and even with high levels of enzymes, high percentage hydrolysis is still elusive due to biomass resistance. Typically, when enzymes are used in downstream, lower temperature stages, product output is typically of low concentration and slow rates compared to that for starch hydrolysis or fermentation of sugars extracted from sugarcane, due to biological limitations of enzymes, thus increasing overall process costs and typically extending process times significantly. Methods which convert emerging sugars to ethanol, known as simultaneous saccharification/fermentation (SSF) have been under development for about 25 years with up to 2 billion dollars having been spent through the National Renewable Energy Laboratories, but has not yet proven to be a commercial process. Rates of SSF are notoriously slow, thus increasing all related costs.

Concentrated acid, dilute, high-temperature acid combinations, steam, moderate temperature/neutral pH, dry grinding, strong alkali, liquid anhydrous ammonia, high water ratios of lime, conically-shaped rotor-stator tools, a laboratory sonicating device, liquid stream, high-shear, and cavitating devices have been used to attempt to refine biomass economically. But there have been no developments to date that enable such processes to be scaled-up for larger production. There are no unsubsidized or stand-alone economical industrial-scale processes for converting high percentages of native, non-starch biomass, cellulosic portions into glucose, xylose, and downstream products made from those including organic acids or ethanol, ethyl acetate or rumen animal feed, with one exception being a small volume extracted from paper pulping, used for adhesive production. There are few industrial processes that can cost effectively dissolve biomass to produce adhesives or bioplastics to compete with petroleum based feedstock. The method currently being utilized to produce chemical precursors from biomass for adhesives or bioplastics are achieved by extracting oligomers and monomers of glucose, xylose, arabinose, galactose and other trace sugars from the paper pulp industry as "black liquor", as well as protein and amino acids. Black liquor methods require a refining step to remove problem compounds.

SUMMARY OF THE INVENTION

The present invention is a method for refining native biomass to extremely fine and highly disrupted particles using high shear and/or cavitation in combination with high temperature and high or low pH conditions which dissolve biomass to a high percentage. The method of the present invention results in a high percentage of hydrolysis, in many cases near theoretical levels, in short residence times while minimizing inputs over other methods, using low chemical inputs, and optionally with no chemical inputs in certain stages compared to existing processes. The method of the present invention also uses minimal electrical energy inputs and conserves heat energy within the process and reduces equipment requirements while producing concentrated products.

According to the present invention, there is provided a slurry method and equipment for creating biomass having extremely small particle sizes and extensive internal surface area. The method enables dissolved products to be converted into various chemicals, adhesives, plastics, gases, ruminant animal feed and protein/amino acid concentrates.

Hemicellulose hydrolysis can optionally be achieved by combining high temperature with plant acids from acetyl groups without the addition of mineral acids or bases. The hemicellulose products are separated from the remaining cellulose. The cellulose can then be further refined within the high temperature process, combined with low levels of base and acidic chemicals, or extracted for refinement with cellulase enzymes and/or for feeding to ruminant animals such as cows and sheep, or may be used for direct microbial conversion to various biochemicals or for gasification.

BRIEF DESCRIPTION OF THE DRAWINGS

Other advantages of the present invention are readily appreciated as the same becomes better understood by reference to the following detailed description, when considered in connection with the accompanying drawings wherein.

DETAILED DESCRIPTION OF THE INVENTION

Figure 1:
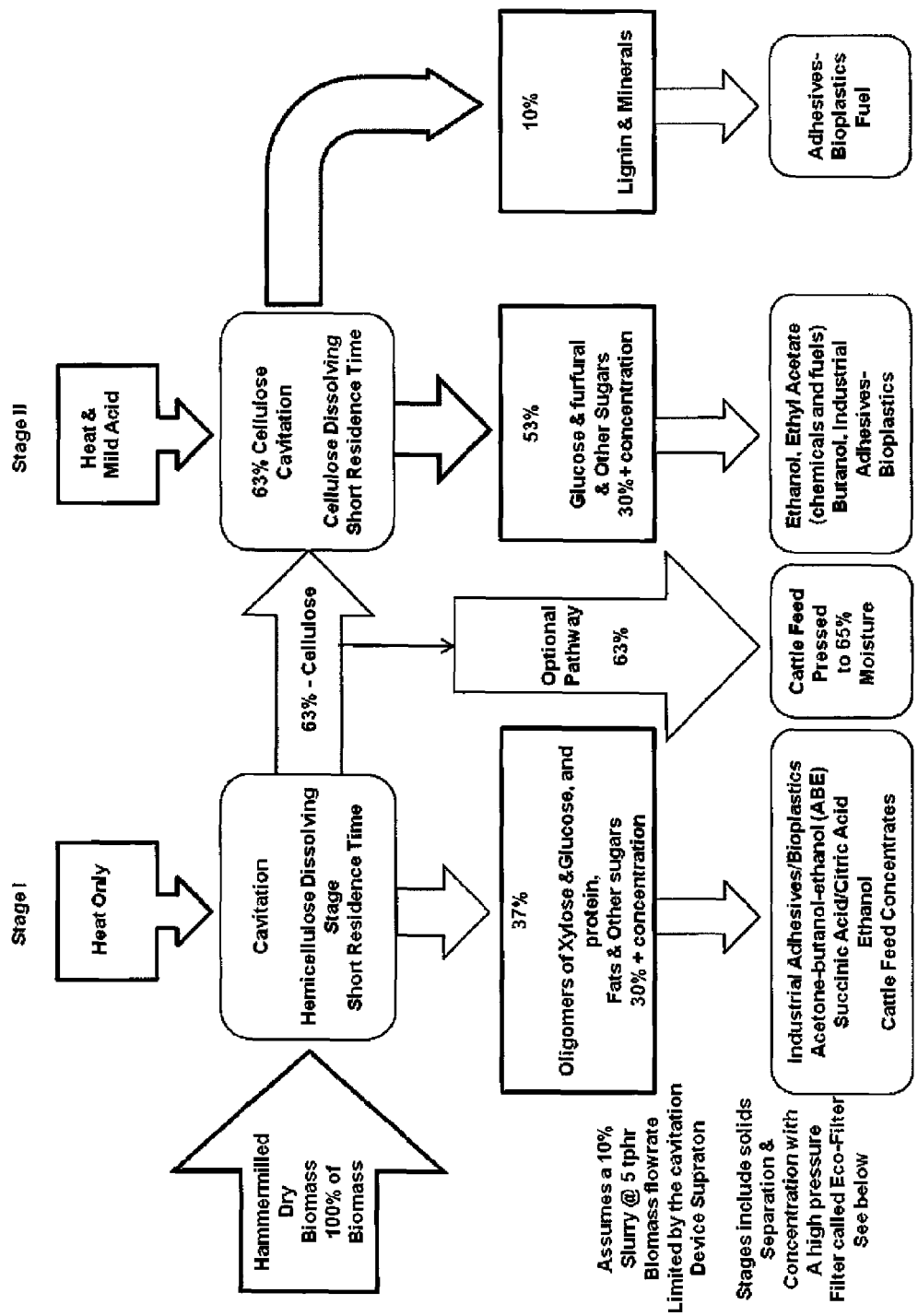
FIG. 1 is a flow chart depicting the method of the present invention.
Figure 2:
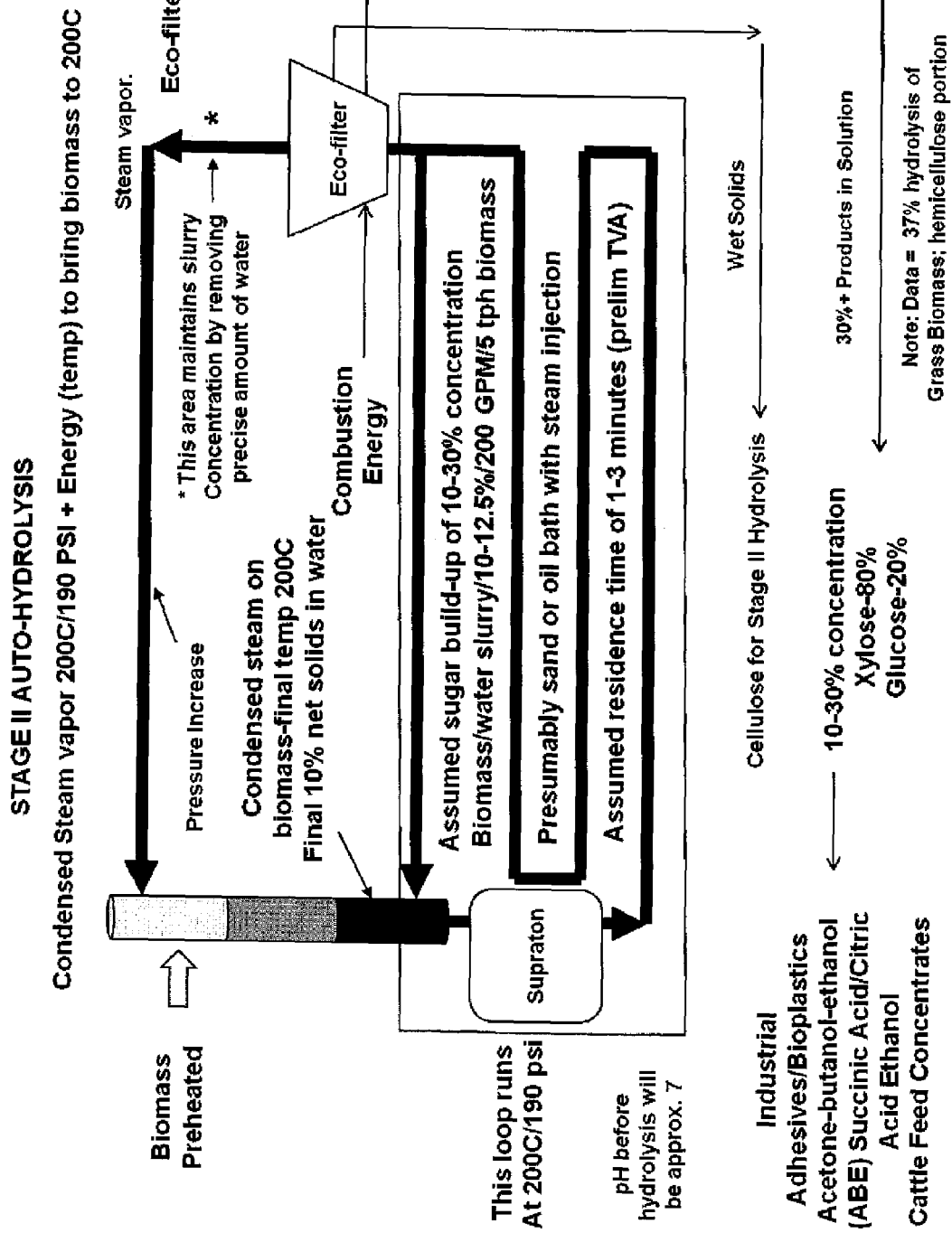
FIG. 2 is a flow chart depicting the auto-hydrolysis stage of the method of the present invention.
Figure 3:
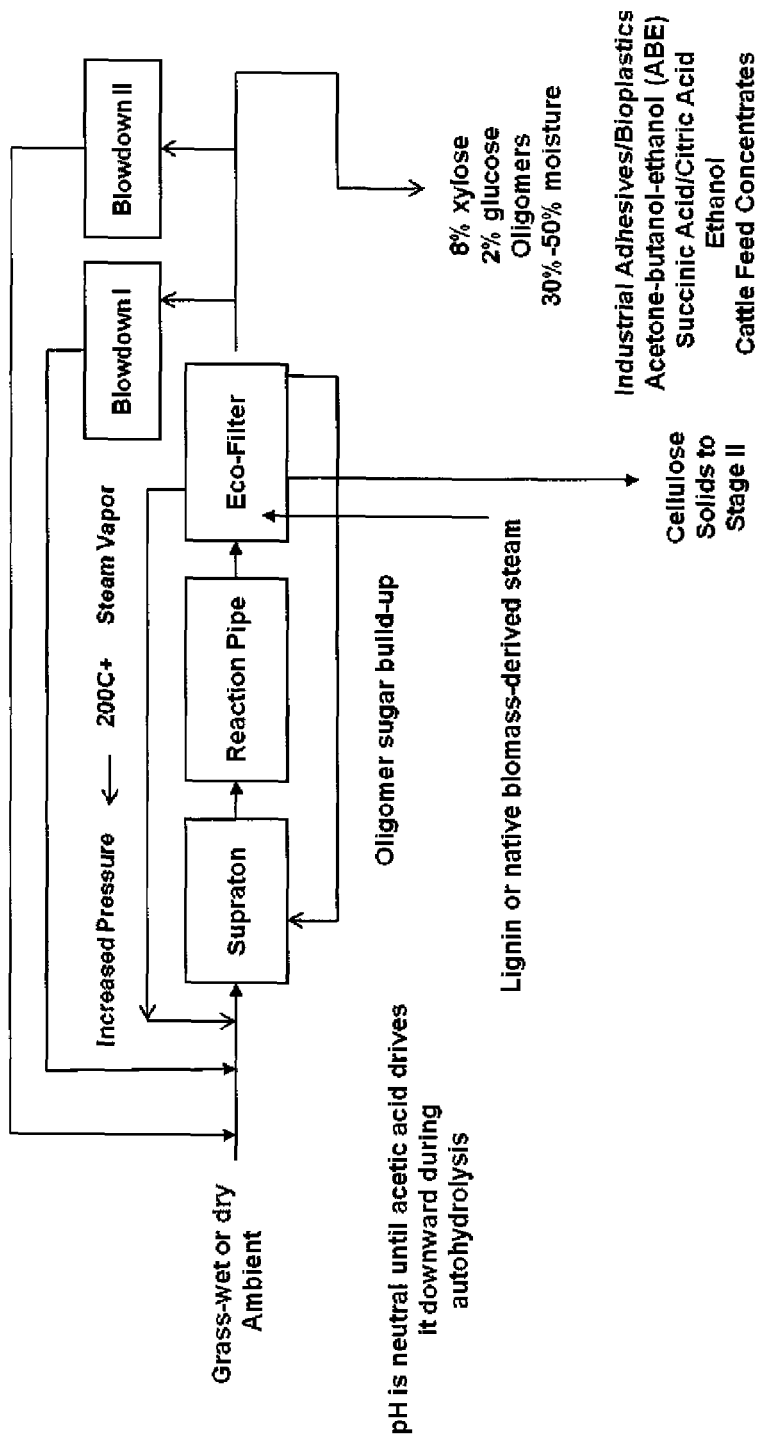
FIG. 3 is a flow chart depicting the xylose-glucose-oligomer concentration stage of the method of the present invention.
Figure 4:
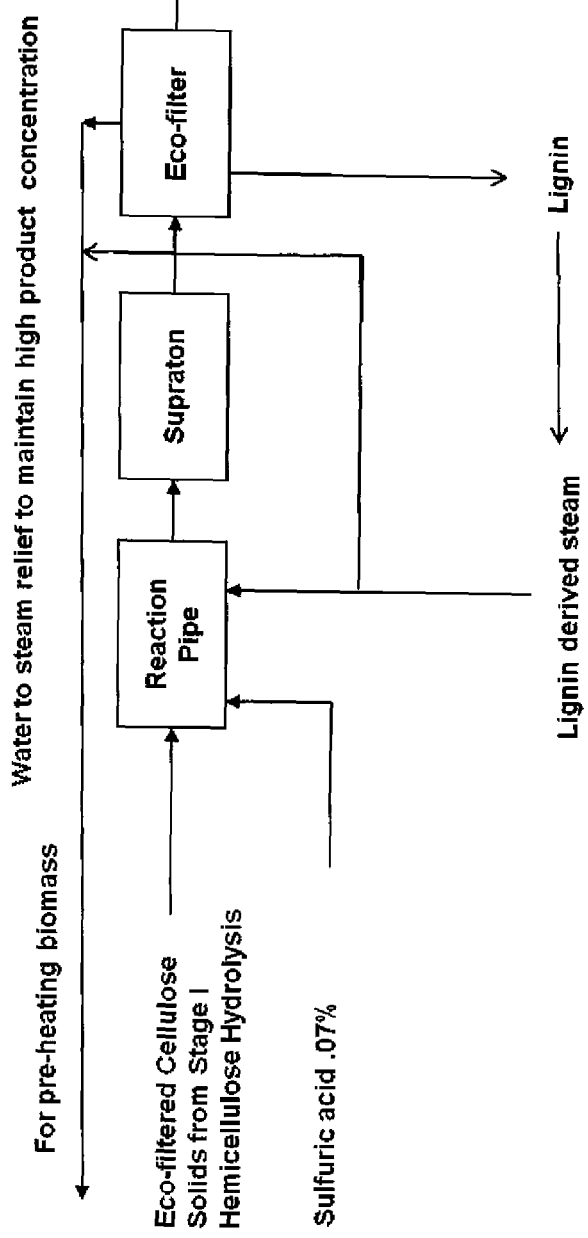
FIG. 4 is a flow chart depicting the cellulose hydrolysis stage of the method of the present invention.

The present invention provides methods that utilize energy savings steps for treating and hydrolyzing biomass while creating very fine particles possessing extensive internal surface area. A wide range of conditions including high temperatures, acids or bases, and optionally using no added acids or base chemicals, with short hydrolysis times and high product concentrations are employed to convert high percentages of biomass to dissolved products in short timeframes.

As used herein, the term "biomass" includes any organic matter (whole, fractions thereof, and/or any components thereof) available on a renewable basis, such as dedicated energy crops and trees, agricultural food and feed crops, agricultural crop wastes and residues, wood wastes and residues, aquatic plants, animal wastes, municipal wastes, and other waste materials. Additionally raw materials include, but are not limited to, cellulose-containing materials, native or treated, such as corn-fiber, hay, sugar cane bagasse, starch-containing cellulosic material such as grain, crop residues, newsprint, paper, raw sewage, aquatic plants, sawdust, yard wastes, biomass, including by not limited to pretreated biomass, components thereof, fractions thereof, and any other raw materials or biomass materials known to those of skill in the art. Lignocellulose-containing fiber, and in the case of grains, includes starch, herein referred to as "biomass", can be refined into sugars, protein, and lignin, and chemicals for gasification into methane or hydrogen production. Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products. The market for sugars, including oligomers and monomers of glucose and xylose, chemicals and fuels made from them, and arabinose, fats, oils, lignin, is in the tens of billions of dollars per annum, and may ultimately rise to as high as $100-200 billion per annum worldwide as oil supplies dwindle and other factors affect existing fuel supply. With oil prices rising with the potential to rise even further, the demand for an alternative to gasoline and diesel is growing.

High percentage hydrolysis can be achieved in slurry form at temperatures of 160° C. to 300° C., in one or more stages. Prior to high temperature stages used to dissolve other biomass components, one stage can optionally include protein and amino acid extraction at lower temperatures during the application of high shear and/or cavitation, with either chemicals or protease enzymes to dissolve protein which is removed by filtration or other methods. Removing native biomass protein helps insure prevention of Maillard reactions which result from a combination of high temperature, sugar, acidic or base conditions and amino acids which are produced from protein hydrolysis.

On many substrates, high shear and/or cavitation can be accomplished using inline homogenizer devices, without applying chemicals, to achieve a percentage biomass hydrolysis of between 15%-52%, which consists primarily of hemicellulose components xylose, some glucose, tannins, trace sugars, fats, some lignin, some acetic acid, some minerals and other trace elements. The remaining solids may be extracted using an Eco Self Cleaning Filter, a fine mesh separation system (sold by Russell Finex, Inc., Pineville, N.C.), after hemicellulose hydrolysis and separated for further high temperature and chemical treatment, or may be fed to ruminant animals or dissolved with cellulase enzyme cocktails after extraction from the high temperature process. Alternately, the filtered solids can remain in the slurry as the slurry temperature is maintained or increased, with and without the application of additional high shear and/or cavitation, and with the addition of acid or base mineral chemicals or anhydrous ammonia or ammonium hydroxide or other alkaline mineral chemicals to achieve a high percentage of biomass hydrolysis.

Biomass in the heated slurry in any stage can optionally be subjected to rapid pressure changes, high shear and cavitation combined with all of the possible combinations outlined above, for short residence times, thereby disrupting and hydrolyzing the cell structure of the biomass while minimizing degradation products which can inhibit downstream fermentation processes or which can create offensive smells for animals being fed the treated biomass. Also provided is a device or devices and parameters for use of a device or devices for performing the method, wherein the device includes a high shear and/or cavitating and cell structure disrupting device disposed within the high shear and/or cavitating device for creating extreme surface area and disrupting the cell structure and exposing the internal cell.

The method renders biomass components into its sub-components of protein and/or amino acids, oligomers and/or monomers of glucose and xylose, other sugars, tannins, acetic acid and lignin, while isolating and/or using lignin for adhesives, bioplastics and energy production, recovering minerals, and recovering ash to be used in concrete and other products as a binder, making all of these amenable to further refining into chemicals, gas, adhesives, plastics, polymers, and wood composites.

In the present invention, combinations of high shear and/or cavitation, temperature and pH conditions and passageway sizes can be optimally combined in multiple sequential stages to minimize cost inputs. The present invention also provides devices, mechanical operating parameters within devices, shapes of components of such devices, passageway sizes, chemicals, chemical concentrations, pH conditions, pressures, a range of higher temperatures and residence times for performing the method described above, wherein the devices include liquid stream, high-shear and cavitating devices and cell structure disrupting devices within the high shear and/or cavitating devices for disrupting the cell structure and exposing valuable components within the cell to heat, chemicals and dissolving enzymes, operated at various ranges of conditions and configurations depending upon substrate and target rates and yields of hydrolysis for commercial purposes.

The phrases "cell disrupting device", high-shear device, or cavitation device as used herein are intended to refer to a device capable of creating extreme surface area on or inside biomass, and under the right conditions outlined herein, of disrupting the gross and primary cell wall and dissolving most components of biomass, leaving mainly un-dissolved or re-dissolved lignin, and minerals. Such devices can be called interchangeably, mixer-pump-homogenizer, and other names employed by individual vendors. A mixer-pump-homogenizer is a high shear, sometimes cavitation-inducing, rotor-stator device capable of mixing, pumping and shearing slurries, to prepare for following stages using advanced versions of cavitation devices, requiring small entry level particle sizes to avoid plugging in single stage or multi stage devices. The inline mixer-homogenizer pump reduces particle size sufficiently to allow smooth passage through a finer sized nozzle device with holes small enough to induce extreme shear and/or cavitation, preferably below 2 mm in size, but can be larger depending on overall conditions. Examples of this type of device are the HED™ manufactured and marketed by Ika Works, Inc. of Wilmington, N.C. Custom designs based upon multi-stage Supraton type machines, using larger slots or round holes can produce very fine and disrupted particles from longer field chopped fibers. The inline mixer-grinder pump can have conical, tooth and chamber, square or rectangular type tools, and can also have nozzle tools larger than 2 mm to induce even greater shear than the tooth and chamber design tools to prepare for additional treatment under the most intense shear and cavitation conditions in single or multi-stage devices.

Once biomass has been adequately reduced in particle size employing one or more of the tools and methods described herein, the slurry is passed through a high-shear or high shear and cavitating device with nozzle holes typically less than 2 mm in diameter, preferably at tip speeds of approximately 50-200 feet per second, or at higher speeds in newer systems. The device or devices may be employed prior to high temperature or within high temperature systems. The term "tip speed" in describing the workings in a rotor-stator device is defined as the rate at which a point on the rotor, of a rotor-stator device, passes a fixed point on the corresponding stator, if that pathway was laid out in a direct line and measured by feet or meters. Preferred is a tip sped in excess of 120 feet per second, with an especially preferred range of 140 feet per second to 200 feet per second. This step may be repeated, as a pretreatment or within a high temperature process with and without added chemicals, depending upon the type of biomass being treated or portion of biomass being dissolved, specifically related to lignin content and in some cases, silica content. As the biomass slurry is pumped under pressure into the high shear or cavitation tools' chamber by the mixer-grinder-pump, it encounters one or multiple concentric layers of the tools in the chamber as the slurry is forced out radially.

The pressure on the slurry creates the lateral radial force as it is pumped into the chamber by the mixer-grinder-pump and by the centrifugal force created by the spinning rotor. The slurry passes through the gaps between the teeth or through the nozzle as the rotor spins past the gaps or nozzles of the stator. In multi-stage designs, the result is a pulsing flow with a rapid succession of compressive and cavitational, expansion-compression forces. The lignocellulosic material in the slurry is subjected to these repeated forces, as the centrifugal force accelerates it through the gaps and holes toward the outer edge of the chamber. As the slurry moves towards the outer edge of chamber the centrifugal forces increase, thus intensifying the forces generated in the gaps. In the outer ring or rings, the slurry is forced through a gap or nozzle tool at the highest pressure within the system. The pressure exerted on the slurry is released as the biomass exits the nozzle or nozzles, and results in a violent shear upon, and/or cavitation from without and within the gross and primary cellular structures of the biomass, depending on prescribed conditions. The repeated compressive and decompressive forces create bubbles by way of cavitation in the slurry within extremely intensive energy zones. The heated lignocellulosic gross fibrous structures, and most importantly, the primary cells, are pounded from the outside and blown apart from the inside by the cavitational forces, as the heated water violently vaporizes from within the gross cellular structures and then just as violently re-collapses into liquid with the passing of a rotor. It is calculated that as many as half a billion such events occurs per second in a large-scale cavitation device. Amorphous hemicellulose components are quickly disrupted and dissolved under the temperature and pH conditions outlined above.

The present invention can utilize temperatures from ambient to in excess of 300 degrees Celsius throughout the sequence of processing steps as shown in the attached figures. One advantage to the present invention is minimizing residence time in dissolving hemicellulose to xylose and glucose and other sugars, protein, acetic acid and lignin extract, and cellulose into glucose and other biomass components to convert high percentages of biomass into high quality products.

The present invention generally, but not always, consists of 4 main stages, including 1) initial particle size reduction, 2) hemicellulose hydrolysis and product recovery, 3) cellulose hydrolysis and product recovery, and 4) recovery of lignin.

In a specific example, dry native Biomass is reduced in particle size by a grinding hammermill, or other suitable mill such as the Megamill by Prater Sterling of Bolingbrook, Ill. If wet biomass is used as a feedstock, such as raw, untreated sewage or fresh grass, as examples, a slurry type particle size reduction device such as an HED inline homogenizer type device manufactured by IKA and other companies can be employed to reduce particle sizes. Generally, after a sequence of particle size reduction starting with either the wet or dry method with water added to create a slurry, wet particles are able to be sequentially passed through holes, square, rectangular, or round in high speed slurry homogenizers down to as low as 0.75 mm-0.5 mm. Generally, but not always, once the particles can pass an opening of 1.5 mm, the hole is round as a practical engineering matter. As the slurry containing the biomass particles passes through a hole, particles become ever smaller and become internally disrupted as extreme shear and cavitation is induced in the smaller holed tools within the homogenizer device(s). The ultimate small hole size within such a device is limited by engineering for viscosity, solids loadings, biomass type, age of biomass and other factors. Preferred is a final homogenizer hole size of no smaller than 0.75 mm, although in some applications a smaller hole would be practical. In certain process configuration, larger holes provide sufficient shear and cavitation to achieve high levels of hydrolysis. On many substrates, a hole size as large as 2 MM or larger is suitable for an effective dissolving process when combined with other inputs such as heat and chemicals.

The second stage in a preferred embodiment is hemicellulose hydrolysis. Once a generally smaller particle size is reached employing the above described method(s), the dry particles, or wet particles are introduced into a slurry reaction pipe, generally with the slurry reaching an average temperature of between 150° C. and 300° C. Once the fine particle biomass slurry is within the hemicelluloses hydrolysis pipe or other reaction vessel, the slurry passes through machines that generate extremely high shear and cavitation. Further, when cavitation occurs within the temperature range of 150° C.-300° C., acetyl groups become acetic acid to drive the dissolving of the hemicelluloses fraction of the biomass. By applying cavitation under the above prescribed conditions, rates of hydrolysis are extremely fast, ranging from seconds to less than 5 minutes, depending on substrates. As this stage does not degrade reduction products of xylose and glucose oligomers, extended times beyond 5 minutes, when required on more recalcitrant substrates, can be employed to achieve high levels of hemicelluloses hydrolysis. A typical process goal for treatment in the Supratron, as one example of a high shear and/or cavitation device, is 10% wt to 12 wt % biomass slurry at 190 psig and 200° C. (392° F.), although much lower concentrations may be practical on some low cost substrates. Some substrates with higher lignin and ash content may require lower concentrations, higher temperatures, and other more aggressive inputs, while lower lignin materials can flow well at higher concentrations and hydrolyze faster with less aggressive inputs.

After pre-ground dry biomass is augured from a storage silo into a slurry tank, the biomass is mixed with water and low-pressure (atmospheric) recycled steam and condensate. Alternately, slurries containing biomass, such as raw sewage, can be the starting feedstock. This technique recovers the atmospheric steam and condensate heat outside the high-pressure high-shear, cavitation loop in which a Supraton type device is employed within. The low-pressure, recycled steam is at atmospheric pressure and is left over from downstream flashes of high pressure steam. This atmospheric steam is directly injected sub-surface into the slurry feed tank to minimize vapors vented from the tank. The condensate is the hot atmospheric condensate from these same flashes.

Slight nitrogen pressure is applied to the feed slurry tank to condense any vapors produced from heating the biomass. However, the pressure is maintained below 15 psig. The pressure is set at 28 psia or about 13 psig. At this pressure the slurry will heat up to about 228 F. prior to pressurization. An agitator is shown to keep biomass suspended and provide more homogenous slurry. The high-pressure steam mentioned above is created using recovered process water to a boiler or heat-generating device that provides the heat necessary to achieve 392° F. In the preferred method of applying steam or condensed steam generated from the reaction pipe system wherein energy is added while pressure is maintained, a dual function of removing water from the reaction pipes to maintain high product concentration in the reaction pipes or other chambers, and transferring the water to the incoming cooler biomass conserves energy within the overall process. Some type of fuel must be provided at a rate of approximately 9 MMBtu/hr. The cavitation device operating pressure is achieved by a progressive cavity, such as a Moyno-type pump. The discharge pressure is set to achieve a pressure of 220 psig at the inlet to the cavitation device. The assumed pressure drops across the two heat exchangers is 5 psi each resulting in a pump discharge of 230 psig (245 psia). This pressure is required to keep the water in the slurry from flashing at 392° F.

Two heat exchangers are provided to recover heat from downstream product flash-drying equipment and provide a 392° F. feed to the Supratron treatment area of the system. The first heat exchanger recovers heat from steam flashed from 210 down to 100 psig. The second heat exchanger uses steam produced by a boiler or heat-generating device. The high-pressure condensate from both exchangers is flashed in two stages down to atmospheric pressure and retuned to the feed slurry tank. The condensate from these exchangers is not flashed in the product flash-drying devices because this adds water to the product. The Supratron and reactor/dissolver produce the sugars-based product that is fed to the Eco-Filter. The pipe reactor dissolves the hemi-cellulose portion of the biomass. Reactor residence time can be calculated for a given pipe diameter and length.

The Eco-filter hemicellulose-based sugar product for chemical production, including optional use as an oligomeric sugar/tannin-based adhesive product, or bioplastics product, plus water, is routed to a boiler or heat-generating device where fuel is applied or consumed by the process to produce the heat necessary to heat the feed to 392° F. The steam from this boiler is directed to the second exchanger mentioned above while the boiler bottoms are routed to the first product flash-dry stage. The boiler produces 235 psig (250 psia) steam at 401° F. to provide an 9° F. approach in the second exchanger. The first flash reduces the pressure from 235 psig to 100 psig (115 psia). The steam from this flash goes to the first feed heat exchanger. The bottoms are product flow to the second flash. The second flash reduces pressure from 100 psig to atmospheric pressure. The atmospheric steam from this flash is sent back to the low-pressure slurry feed tank outside the pressurized loop. The bottoms from this flash contains product at about 10 wt % product and may require further drying.

The cellulose solids from the Eco-filter are sent to a mixer where sulfuric acid or a selected base chemical is added. This stream is about 65 wt % water. The acid is added in a ratio of 0.009 lb acid per lb of total mass, while a range of base chemicals can be applied depending on the desired rate and degree of refining desired. Depending on the type of biomass, acid loadings can range from 0.025% to 2%, with a preferred range of sulfuric acid of 0.5%-0.9%. Hydrolysis progresses very quickly with high percentages of hydrolysis taking between a few seconds to 5 minutes, preferably in less than 1 minute to minimize degradation to hydroxy-methyl furfural and other fermentation inhibitors. Application of high shear and cavitation within the reaction pipe containing mild acid accelerates the reaction to where some substrates will dissolve in less than 1 minute to commercially important percentages.

The cellulose is dissolved in a pipe or tank reactor. After the cellulose is dissolved with acid, ammonia is added (one mole of NH3 per mole of sulfuric added), or a reversed formula with base chemicals and neutralizing acid are employed. A 10%-30% aqua ammonia solution is utilized for acid neutralizing, although higher concentrations can be employed in some strategies. Two high pressure metering pumps are required for all additives.

The slurry now passes through two pressure-reducing flashes similar to the flashes discussed above for the hemicellulose product. The high pressure flash produces more vapor for the first heat exchanger, while the atmospheric flash reduces the pressure further so the steam and condensate can be added to the low-pressure feed slurry tank that is outside the high-pressure loop. The cellulose-based product is about 56% water and may or may not require further processing.

Un-dissolved biomass may be further processed at the same temperature with the addition of other inputs. In one preferred embodiment, un-dissolved solids, consisting primarily of cellulose and lignin, are separated by a filtration system, for example using a filter such as an Eco-Filter. The solids must be transferred to 1 atmosphere for use in downstream processes or as a stand-alone product which can be utilized in many products including bio-based adhesives and bioplastics, and fuels. All of the inputs above are preceded or followed by and/or, combined with high shear or high shear and cavitation combined under a range of equipment tip speeds and pressures, induced under a wide range of elevated pressures at the entrance of specially designed and sized openings, and low exiting pressure zones within systems. The above described process conditions are one example. All inputs can be combined in multiple ratios depending on substrate, desired results and differing product extraction strategies.

The present invention can also be used to extract protein from biomass to prevent Maillard reaction degradation within the overall process, when desired and when applicable, and for producing protein, polypeptide or amino acid products from those extractives. The method of the present invention creates, as a co-product, highly digestible ruminant feed, once extracted, either as a partially hydrolyzed or whole pretreated product. The Maillard reaction, also known as non-enzymatic browning, involves the thermal reaction between an aldose or a ketose and alpha-amino acids or amino acid residues in proteins to afford a resulting Schiff base. The Schiff base residues may undergo subsequent rearrangement to form a more stable structure known as the Amadori product. Further reaction may lead to the formation of indigestible melanoidins. Utilization of the early stages of the Maillard reaction leads to amino acid or protein residues that are protected from fermentation within the rumen microflora environment and therefore tend to escape fermentation in the rumen to be metabolized in the post-rumen portions of the ruminant digestive system.

In one embodiment utilizing protein containing biomass, biomass protein is dissolved in high temperature conditions when combined with acid, and sugars being produced which become "caramelized" in a "Maillard reaction", thus a loss of sugars and protein takes place if the objective is capturing fermentable sugars. While the Maillard Reaction is advantageous as one method for producing adhesive precursors and bioplastics, for sugar production to produce fermented chemicals, extracting or removing protein is an important, even critical option before hydrolysis so as to prevent their loss to the Maillard reaction. Applying protease enzymes at low temperature for extraction is employed to remove protein before high temperature treatment with mild acid to prevent the Maillard reaction. Pretreated biomass using the present method enhances enzymatic extraction of protein due to enhanced surface area. Biomass is mixed with water, if it is not already in slurry form. The slurry is first subjected to high temperature extraction and coagulation, or alternately to protease enzymes, potassium chloride, mild acid base or combinations of these or in sequence to remove protein from biomass when it exists. Once optimal protein has been extracted, the slurry is centrifuged or filtered, protein and/or amino acids are separated and recovered, and the supernatant recycled as feed water for the next biomass. Proteins or amino acids are extracted from the supernatant by industrial chromatography, flowed through an active organic process which can metabolize them, or other method for removing the protein and amino acids as product for sale as animal feed, or as a human nutritional product. Large scale tropical processing of biomass utilizing the present invention will produce new, unprecedented volumes of protein, polypeptide and/or amino acids to add to local diets notoriously deficient in protein based essential nutrients.

The method of the present invention can also be used for blending final dissolved or partially dissolved biomass products with plastics to create unique structural materials including railroad ties, body parts, and building materials, to name a few.

The present invention provides for a fast, complete, and/or nearly complete hydrolysis of biomass, employing minimal or no chemical and minimal mechanical inputs, while selectively minimizing degradation of substrate to products such as hydroxymethyl furfural and other less desirable products, when such products are not desired. Conversely, in higher value product strategies, furfural and other products can be produced, with one example being the production of hydroxymethyl furfural for use as a component of adhesives or bioplastics. The method produces glucose and other products in high concentrations, which are valuable in fermentations where low concentrations of product are economically problematic. The method of the present invention can optionally produce fermentable sugars and other products without the use of expensive enzymes, the use of which is rate and product concentration limiting. The method also can remove fermentation inhibitors that can be produced during biomass refining.

The method of the present invention can also be used for enhancing production of "syngas" through high temperature pyrolysis, or gasification. The method can also be used for gasification of waste products.

The method of the present invention involves conserving heat energy in a combined engineered pathway of increasing product build-up in final product extraction from high pressure zones, to utilize energy employed in the build-up step for pre-heating fresh incoming biomass to hydrolysis temperatures at which enzymes are not employed, while increasing rates of hydrolysis, thus employing lower energy for mechanical processing and achieve high conversion percentages when applying low levels of mineral and ammonia catalysts.

Throughout this application, author and year and patents by number reference various publications, including United States patents. Full citations for the publications are listed below. The disclosures of these publications and patents in their entireties are hereby incorporated by reference into the application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of refining lignocellulosic biomass comprising cellulose and hemicellulose fractions, the cellulose and hemicellulose fractions comprising cells having structure, the method comprising the steps of:

(a) applying high shear and cavitation to a slurry containing the biomass to disrupt the cellular structure of the cellulose and hemicellulose fractions of the biomass;

(b) subsequent to step a, removing native biomass protein from the slurry; and (c) subsequent to step b, heating the slurry to a temperature of between 150° C. and 300° C. for a duration sufficient to hydrolyze a high percentage of the biomass.

2. The method of claim 1, wherein the protein removal step comprises adding protease enzymes to the slurry.

3. The method of claim 1, wherein the protein removal step comprises adding potassium chloride to the slurry.

4. The method of claim 1, wherein the protein removal step comprises adding acid to the slurry.

5. The method of claim 1, wherein the protein removal step comprises adding a base to the slurry.

6. The method of claim 1, wherein the protein removal step comprises subjecting the slurry to high temperature extraction and coagulation.

7. The method of claim 1, wherein the protein removal step further comprises removing amino acids from the slurry.

8. The method of claim 1, wherein step (c) further comprises applying high shear and cavitation to the heated slurry.

9. The method of claim 1, wherein the application of high shear and cavitation in step (a) comprises passing the biomass slurry through a high shear and cavitating device with nozzle holes less than 2 mm in diameter, and operating at a tip speed of at least 120 feet per second.

10. The method of claim 9, wherein the application of high shear and cavitation in step (a) comprises passing the biomass slurry through a high shear and cavitating device with nozzle holes less than 2 mm in diameter, and operating at a tip speed of at least 140 feet per second.

11. The method of claim 10, wherein the application of high shear and cavitation in step (a) comprises passing the biomass slurry through a high shear and cavitating device with nozzle holes less than 1.5 mm in diameter, and operating at a tip speed of at least 150 feet per second.

12. The method of claim 10, wherein the high shear and cavitating device operates at a tip speed of at least 200 feet per second.

13. The method of claim 1, further including a step of adding a chemical to the biomass slurry prior to or during step (c) to accelerate the hydrolysis of the biomass.

14. The method of claim 13 wherein the chemical is selected from the group consisting of mineral acids, anhydrous ammonia, ammonium hydroxide, and alkaline mineral chemicals.

15. The method of claim 14, wherein a mineral acid is added to the biomass slurry to produce an acid loading of less than 2% to accelerate the hydrolysis of the biomass.

16. The method of claim 1 wherein the biomass slurry is heated to a temperature of at least 200° C.

17. The method of claim 1 wherein the biomass comprises hemicellulose, and none of the following chemicals are added to the slurry: mineral acids, mineral bases, anhydrous ammonia, ammonium hydroxide, and alkaline mineral chemicals.

18. The method of claim 1 wherein no chemical is added to the biomass slurry during step (c).

19. The method of claim 8 wherein step (c) is performed for less than five minutes.

* * * * *